United States Patent [19]

Muzyczka et al.

[11] Patent Number: 5,139,941
[45] Date of Patent: Aug. 18, 1992

[54] AAV TRANSDUCTION VECTORS

[75] Inventors: Nicholas Muzyczka, Stony Brook, N.Y.; Paul L. Hermonat, Bethesda, Md.; Kenneth I. Berns, Mamaroneck, N.Y.; Richard J. Samulski, Princeton, N.J.

[73] Assignee: University of Florida Research Foundation, Inc., Alachua, Fla.

[21] Appl. No.: 785,224

[22] Filed: Oct. 25, 1991

Related U.S. Application Data

[63] Continuation of Ser. No. 793,543, Oct. 31, 1985, abandoned.

[51] Int. Cl.⁵ .................. C12N 15/63; C12N 15/86
[52] U.S. Cl. ................... 435/172.3; 435/320.1; 935/32; 935/57
[58] Field of Search ............ 435/69.1, 70.1, 70.3, 435/172.1, 172.3, 320.1, 240.1, 240.2, 235, 236; 536/27; 935/32, 34, 57, 70, 71

[56] References Cited

U.S. PATENT DOCUMENTS 4,797,368  1/1989  Carter et al. .................. 435/320.1

OTHER PUBLICATIONS

Lebkowski et al.; Molec. Cell. Biol., 8:3988 (1988).
Senapathy et al.; J. Biol. Chem., 259:4661 (1984).
Laughlin et al.; Gene, 23:65 (1983).
Mulligan et al.; Science, 209:1422 (1980).
Samulski et al.; J. Virol., 61:3096 (1987).
Labow et al.; J. Virol., 60:251 (1986).
Joyner et al.; Molec. Cell. Biol., 3:2191 (1983).
Joyner et al.; Molec. Cell. Biol., 3:2180 (1983).
Miller et al.; Molec. Cell. Biol., 5:431 (1985).
McLaughlin et al.; J. Virol., 62:1963 (1988).
Tratschin et al.; Molec. Cell. Biol., 4:2072 (1984).
Hermonat et al.; Proc. Natl. Acad. Sci. USA, 81:6466 (1984).
Tratschin et al.; J. Virol., 51:611 (1984).
Tratschin et al.; Molec. Cell. Biol., 5:3251 (1985).

Primary Examiner—James Martinell
Attorney, Agent, or Firm—Kerkam, Stowell, Kondracki & Clarke

[57] ABSTRACT

A hybrid gene vector suitable for introducing foreign DNA into a mammalian cell comprising the foreign DNA ligated to an AAV genome; a method of constructing the hybrid gene vector; a method of transducing foreign DNA into mammalian cells comprising infecting the cells with the above hybrid gene vector and a method of rescuing foreign DNA from mammalian cells utilizing helper virus.

10 Claims, 4 Drawing Sheets

AAV TRANSDUCTION VECTORS

The work leading to the completion of the present invention was supported by National Institutes of Health Grants IR01GM31576 and R01AI16326 and National Institutes of Health predoctoral traineeship (5732A107110). The U.S. Government has certain rights in this invention.

BACKGROUND OF THE INVENTION

This application is a continuation of application Ser. No. 06/793,543 filed on Oct. 31, 1985, now abandoned.

FIELD OF THE INVENTION

The present invention relates to certain mammalian transduction vectors.

PRIOR ART

Adeno-associated virus-2 (AAV) is a human parovovirus which can be propagated both as a lytic virus and as a provirus [Cukor et al, In: The Paroviruses, ed. K. I. Berns (Plenum, New York, pp. 33-66 (1984); Hoggan et al, In: Proceeding of the Fourth Lepetit Colloquium, Cacoyac, Mexico, (North Holland, Amsterdam), pp. 243-249 (1972)]. The viral genome consists of linear single-stranded DNA [Rose et al, Proc. Natl. Acad Sci., USA, Vol. 64, pp. 863-869 (1969)], 4679 bases long [Srivastava et al, J. Virol. Vol. 45, pop. 555-564 (1983)], flanked by inverted terminal repeats of 145 bases [Lusby et al, J. Virol. Vol. 41, pp. 518-526 (1982)]. For lytic growth AAV requires co-infection with a helper virus. Either adenovirus [Atchinson et al, Science, Vol. 194, pp. 754-756 (1965); Hoggan, Fed. Proc., Vol. 24, p. 248 (1965); and Parks et al, J. Virol., Vol. 1, pp. 171-180 (1967)] or herpes simplex [Buller et al, J. Virol. Vol. 40, pp. 241-247 (1981)] can supply helper function. Without helper, there is no evidence of AAV-specific replication or gene expression [Rose et al, J. Virol., Vol. 10, pp. 1-8 (1972); Carter et al, In: The Parvoviruses, ed. K. I. Berns (Plenum, New York), pp. 67-128, (1983); Carter et al, In: The Parvoviruses, ed. K. I. Berns (Plenum, New York) pp. 153-207 (1983)]. When no helper is available, AAV can persist as an integrated provirus [Hoggan, supra, Berns et al, Virology, Vol. 68, pp. 556-560 (1975); Handa et al, Virology, Vol. 82, pp. 84-92 (1977); Cheung et al, J. Virol. Vol. 33, pp. 739-748; Berns et al, In: Virus Persistence, ed. Mehay et al (Cambridge Univ. Press), pp. 249-265 (1982)].

Integration apparently involves recombination between AAV termini and host sequences and most of the AAV sequences remain intact in the provirus. The ability of AAV to integrate into host DNA is apparently an inherent strategy for insuring the survival of AAV sequences in the absence of the helper virus. When cells carrying an AAV provirus are subsequently superinfected with a helper, the integrated AAV genome is rescued and a productive lytic cycle occurs [Hoggan, supra].

Much of the recent genetic work with AAV has been facilitated by the discovery that AAV sequences that have been cloned into prokaryotic plasmids are infectious [Samulski et al, Proc. Natl. Acad. Sci. USA Vol. 79, pp. 2077-2080 (1982)]. When the wild type AAV/pBR322 plasmid, pSM620, is transfected into human cells in the presence of adenovirus, the AAV sequences are rescued from the plasmid and a normal AAV lytic cycle ensues [Samulski et al (1982), supra]. This renders it possible to modify the AAV sequences in the recombinant plasmid and, then, to grow a viral stock of the mutant by transfecting the plasmid into human cells [Samulski et al, Cell, Vol. 33, pp. 135-143 (1983); Hermonat et al, J. Virol Vol. 51(2), pp. 329-339 (1984)]. Using this approach it has been demonstrated that there exists at least three phenotypically distinct regions (FIG. 1) in AAV [Hermonat et al, supra]. The rep region codes for one or more proteins that are required for DNA replication and for rescue from the recombinant plasmid. The cap and lip regions (FIG. 1) appear to code for AAV capsid proteins and mutants within these regions are capable of DNA replication [Hermonat et al, supra]. In addition, studies of terminal mutants show that the AAV termini are required for DNA replication [Samulski et al, (1983) supra].

Laughlin et al [Gene, Vol. 23(1), pp. 65-73 (1983)] have described the construction of two *E. coli* hybrid plasmids, each of which contains the entire DNA genome of AAV. Laughlin et al, supra, also describe the transfection of the recombinant DNA's into human cell lines in the presence of helper adenovirus to successfully rescue and replicate the AAV genome. See also Tratschin et al, J. Virol., Vol. 51(3), pp. 611-619 and Tratschin et al, Mol. Cell Biol., Vol. 4(10), pp. 2072-2081. Thus, each of these authors present a mechanism for utilizing an AAV genome in a transient expression system. To date, however, no system or vector for permanently introducing foreign DNA into mammalian cells based on AAV has been perfected.

Until the present time the most successful and widely researched viral vectors were the retroviruses. There are numerous disadvantages associated with the use of retroviruses as vectors, however. For the most part, the retroviruses are pathogenic to animals, including humans, and are not sufficiently reliable in that the DNA inserted thereby into foreign cells often do not remain in the loci of transfection. Moreover, the range of hosts suitable for transfection by retroviral vectors is somewhat limited.

It is an object of the present invention to provide novel AAV vectors for the introduction, integration, expression and rescue of foreign DNA in mammalian cells.

SUMMARY OF THE INVENTION

The present invention provides a general purpose AAV based hybrid gene vector; a method of constructing the hybrid gene vector or hybrid gene virus stock; a method for employing the hybrid vector to introduce foreign DNA into a mammalian cell line (hereinafter variously referred to as "recombinant AAV viral transduction" or, simply, "transduction"); the resultant mammalian cell line (hereinafter variously referred to as "transduced cell line" or "transductant"); and a method of rescuing foreign DNA from the "transductants".

According to one embodiment of the invention, there is provided a hybrid gene vector especially adapted for introducing foreign DNA into a mammalian cell line comprising the foreign DNA ligated to an AAV genome.

Another embodiment of the invention comprises a method for constructing the hybrid gene vector comprising ligating the foreign DNA to an AAV genome cloned in a prokaryotic vector plasmid (i.e., AAV recombinant plasmid) and isolating an AAV recombinant hybrid gene vector (or virus) by transfection of the AAV recombinant plasmid into mammalian cells that have also been infected with a helper virus and/or transfected with an AAV helper genome.

A further embodiment of the invention comprises a method of introducing foreign DNA into a mammalian cell by infection thereof with the AAV based recombinant virus (i.e., hybrid gene vector).

An additional embodiment of the invention comprises a method of rescuing foreign DNA which has been introduced into a mammalian cell by infection thereof with a helper virus (i.e., adenovirus or herpes simplex virus) and/or an AAV helper genome.

A final embodiment of the invention comprises the transduced mammalian cells produced according to the above-described method and which contain or carry a recombinant AAV provirus.

It will be understood that by the term "AAV genome" is meant either the entire AAV viral DNA structure or a deletion mutant thereof capable of replication upon infection when complemented in trans by the appropriate AAV genes; and that by the term "AAV provirus genome" is meant an AAV genome introduced into a mammalian cell and residing in a mammalian chromosome.

It will be further understood that by the term "helper virus" is meant a virus or genome that contains genes necessary for the replication of the AAV genome or the production of AAV virus, the most commonly used helper viruses being members of the adenovirus or herpes simplex virus families; and that by the term "AAV helper genome" is meant the DNA or virus form of an AAV recombinant genome which contains genes necessary to promote the replication of AAV recombinant vector DNA or the production of AAV derived recombinant virus stocks.

DETAILED DESCRIPTION OF THE INVENTION

Figure 1:
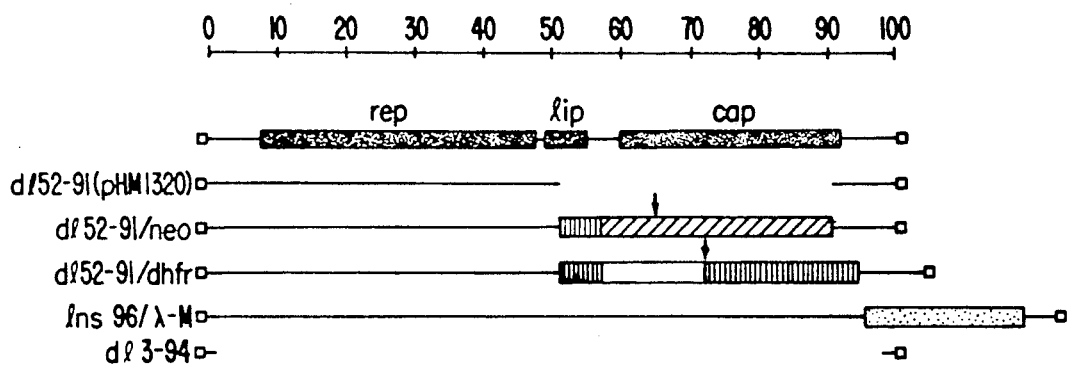
FIG. 1 depicts the physical organization of AAV recombinant genomes.

The present invention is predicated on the discovery of a hybrid gene vector and method or system for reliably inserting foreign DNA into living cells such that the transferred genetic material is stable with respect to the loci of insertion and which is susceptible of expression and rescue. As noted above, the retroviruses are the only vehicles which have been previously employed for this purpose. The above discussed disadvantages, however, have limited their application. The AAV vectors of the present invention have been found to be suitable for transduction of virtually any mammalian cell.

Foreign DNA introduced into mammalian cells according to the AAV transduction method of the present invention remains attached to the AAV proviral genome and comprises a stable and heritable portion of the mammalian cell genome.

The invention is illustrated by the following non-limiting examples wherein the following materials and methods were employed. The entire disclosures of each of the literature references cited hereinafter are incorporated by reference herein.

Human Detroit 6 cells (D3405, hereinafter termed D6) and D5 cells (a D6 derived cell line which is latently infected with wild type AAV and was previously termed B737IIIDV) were obtained from the National Institutes of Health. Human KB cells, 293-31 cells, a human Ad transformed cell line, and mouse L thiymidine kinase negative (tk$^-$) cells were grown as described by [Hermonat et al, supra]. DNA transfections, virus infections, and wild type titer determinations were conducted as described by Muzyczka, Gene, Vol. 11, pp. 63–67 (1980); and Carter et al, Virology, Vol. 92, pp. 449–461 (1979). DNA extractions and Southern hybridization procedures were conducted as described by Muzyczka, supra; Hirt, J. Mol. Biol., Vol. 26, pp. 365–369 (1967); and Southern, J. Mol. Biol., Vol. 98, pp. 503–518 (1975).

The ligation of foreign DNA to the AAV genome cloned in the prokaryotic vector plasmid is achieved according to accepted, conventional practice [T. Maniatis et al, In: Molecular Cloning, A Laboratory Manual (1982) Cold Spring Harbor Laboratory Press, pp. 286–291 and pp. 398–400]. Briefly, vector DNA and foreign DNA are dissolved at a final concentration of 50 micrograms per ml each, in a final volume of 50 microliters. The mixture also contains 10 millimolar ATP, 10 millimolar MgCl$_2$ and 10 millimolar Tris, pH 7.5. After addition of 1 unit of T4 DNA ligase, the reaction mixture is incubated at 15°–25° C. for 1–24 hours to complete ligation.

Any suitable prokaryotic plasmid vector, bacteriophage vector or yeast plasmid vector may be employed.

Any foreign DNA, i.e., any coding sequence capable of expression in eukaryotic cells, may be utilized in the practice of the invention.

The DNA may be ligated into the AAV genome in place of or in addition to the cap, lip or rep coding sequence thereof or in place of or in addition to any AAV DNA sequence excluding the first and last 145 base pairs.

EXAMPLE 1

Ligation of Foreign DNA to an AAV Recombinant Plasmid

Figure 2:
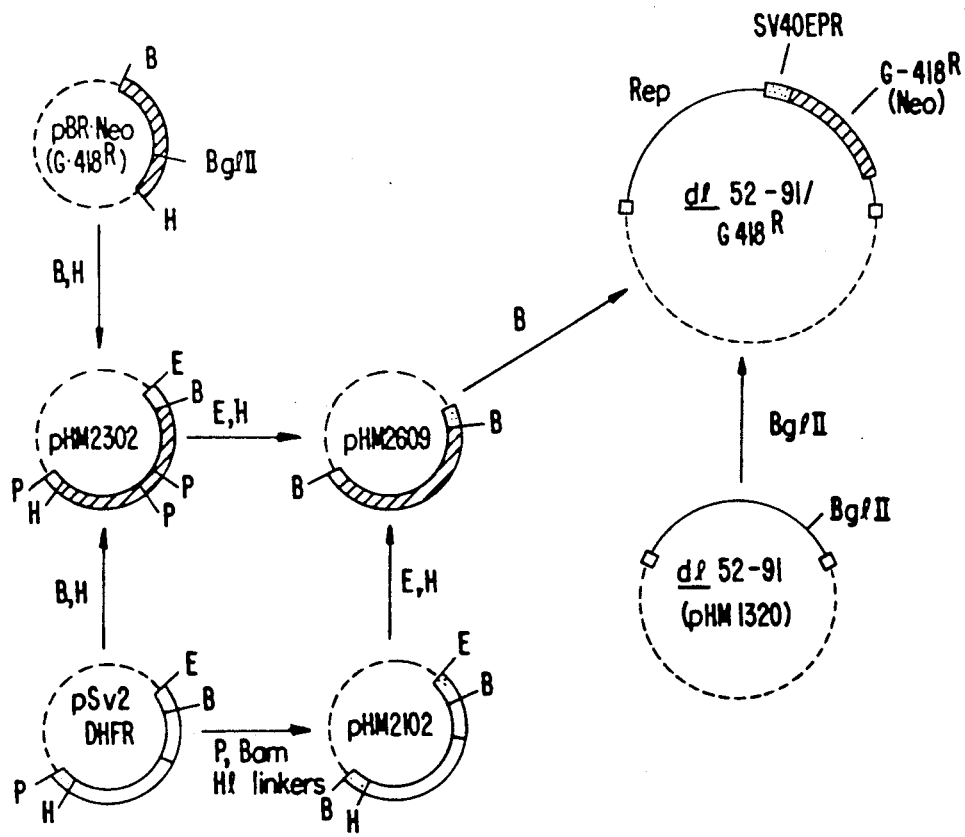
FIG. 2 shows the construction of AAV recombinants.

In order to test the effectiveness of AAV as a tranducing virus, it was necessary to insert a selectable marker into the AAV genome. For this purpose, the neomycin resistance gene under the control of an SV40 promoter [Colbere-Garapin et al. J. Mol. Biol., Vol. 150, pp. 1–14 (1981)] was chosen. The SV40 sequences (SV40 mu 71–65) were excised from the plasmid pSV2-dhfr [Subramani et al, Molec. Cell. Biol., Vol. 1, pp. 854–864 (1981)] and the neomycin resistance gene was obtained from the pBR-neo [Southern et al, Molec. Appl. Genet., Vol. 1, pp. 327–341 (1982)] plasmid (FIG. 2). These two regions were inserted into the AAV deletion mutant, dl52-91, as shown in FIG. 2 and in the orientation shown in FIG. 1. As the name implies, dl52-91 is missing the AAV sequences between map units (mu) 52 and 91 (FIG. 1). It is, therefore, capable of DNA replication but, because it does not contain the AAV capsid genes, it is incapable of producing infectious virus [Hermonat et al, supra]. Based on the orientation of the inserted sequences, the neo gene was expected to be expressed as the result of transcription which was initiated within the SV40 early promoter sequences and terminated at the AAV polyadenylation signal (mu 95). The size of the Dl52-91/neo recombinant was 4.7 kb which is essentially the same as wild type AAV.

A second recombinant in which the mouse dihydrofolate reductase gene was inserted into Dl52-91 was also constructed (FIG. 1). This recombinant, Dl52-91/dhfr, is approximately 6% larger than the wild type AAV genome.

The construction of Dl52-91/dhfr and Dl52-91/neo are illustrated in FIG. 2 and FIG. 2. The plasmids pBR-neo and PSV2-dhfr are described by Southern et al, supra (1982), and Subramani et al, supra (1981). The construction of the parental recombinant plasmid pSM620 from which Dl52-91 was derived is described in detail by Samulski et al (1982), supra. Briefly, AAV DNA was isolated from AAV virus and treated with terminal nucleotidyl transferase in the presence of dCTP. The prokaryotic vector plasmid, pBR322 [Bolivar et al, Gene 2, pp. 95–113 (1977)], was then converted to linear DNA with the restriction enzyme Pstl and tailed with dGTP using terminal nucleotidyl transferase. Finally, the AAV and pBR322 DNA's were mixed and ligated to each other in vitro. The ligated DNA was then transfected into the bacterial host E. coli HB101 and individual clones were tested for the presence of a recombinant plasmid that contained the complete wild type AAV genome. pSM620 was the first such plasmid found and was used as the parental wild type recombinant plasmid for all further studies. pSM620 and all derivatives of pSM620 were cloned and have been propagated as AAV recombinant plasmids in the bacterial host E. coli HB101 [Boyer and Roulland-Dussoix, J. Mol. Biol. 41, pp. 459–472 (1969)].

The construction of Dl52-91 is described in detail by Hermonat et al (1984), supra. Briefly, Dl52-91 was constructed from two other recombinant plasmids ins52 and dl0-91. ins52 contains an 8 bp BglII linker fragment inserted at the HaeIII site of pSM620 at map position 52 on the AAV genome. dl0-91 was constructed from pSM620 by digesting pSM620 with PstI, inserting a BglII linker into the resulting DNA, and subsequently cloning the dl0-91 deletion in HB101. Dl52-91 was then constructed by digesting the ins52 plasmid DNA and the dl10-91 plasmid DNA with BglII and EcoRV, mixing the two digests, treating them with DNA ligase and cloning the ligated DNA in HB101. One of the resulting clones contained the Dl52-91 deletion plasmid.

The plasmid dl3-94 was derived from the plasmids dlb 3-23 deletion and dlb 49-94. dl3-23 was derived by partially digesting pSM620 with BstN1 and inserting a BglII linker at the site of cleavage. dl49-94 was constructed by adding BglII linkers to the 1700 bp HinfI fragment of pSM620 (containing AAV map units 94 to 100 and adjacent pBR322 sequences) and digesting the products with EcoRV and BglII. This restriction fragment mixture was then ligated to a BglII-EcoRV double digest of ins49. ins49, in turn, had been constructed by inserting a BglII linker at the BstN1 site of pSM620 at AAV map position 49. Finally, dl3-94 was constructed by ligating together a mixture of dl3-23 and dl49-94 after they had been digested with BglII and EcoRV.

In all cases in which a BglII linker was inserted at a restriction enzyme site which leaves 5' or 3' single-stranded overhangs (namely, Pst1, BstN1, Hinfl) the overhang was removed prior to ligation of the linker by treating the digested DNA with T4 DNA polymerase in the presence of all 4 deoxynucleotide triphosphates.

With the exception dl3-94, a more complete description of the construction of all of the above-mentioned AAV recombinant plasmid derivatives of pSM620 is contained in Hermonat et al (1984), supra. In addition to their descriptive names (ins49, dl3-94) some of the above-mentioned AAV plasmids are also known by their initial laboratory isolation numbers. These are noted in parentheses below: dl52-91 (pHM1320), ins52 (pHM347), dl3-94 (pHM3902), dl3-23 (pHM1515), dl4-9-94 (pHM3305), ins49 (pHM1523), dl52-91/neo (pHM1320/neo).

Ins96/λ-M was derived from the plasmid pSM620XbaI, which is a derivative of pSM620 [Samulski et al (1982), supra] and which contains an Xba1 linker inserted at AAV mu96. The Xba1 site of pSM620XbaI was converted to a BglII site by inserting a BglII linker and the resulting plasmid was called ins96(pHM2904). Finally, a 1.1 kb Sau3A1 bacteriophage λ fragment was inserted into ins96 to produce ins96/λ-M.

Figure 3:
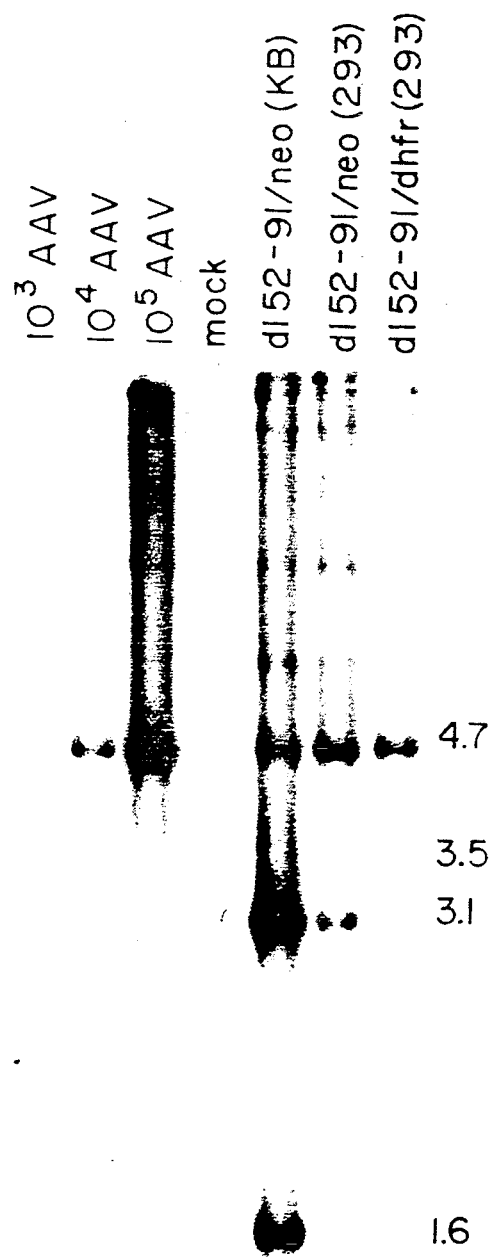
FIG. 3 depicts a comparison of wt and recombinant DNA replication.

To determine if the recombinant plasmids dl52-91/neo and dl52-91/dhfr could replicate, the two plasmids DNA's were transfected into Ad2-infected human cells. As expected, both the neo and the dhfr recombinants were found to replicate to approximately the same extent as the wild type AAV (FIG. 3). Digestion with BglII (an enzyme which does not cut wt AAV) of the DNA harvested from cells after transfection with the dl52-91/neo recombinant plasmid confirmed that it was neo recombinant DNA (FIG. 3).

EXAMPLE 2

Preparation of AAV Recombinant Virus Stock (i.e., Hybrid Gene Vector or Neo/transducing Virus Stock)

In order to grow a Dl52-91/neo viral stock it was necessary to supply the missing AAV capsid gene products in trans. Initial attempts to isolate a stock by complementation with the wild type plasmid pSM620 were unsuccessful because of a strong bias toward packaging the wild type genome.

Figure 4:
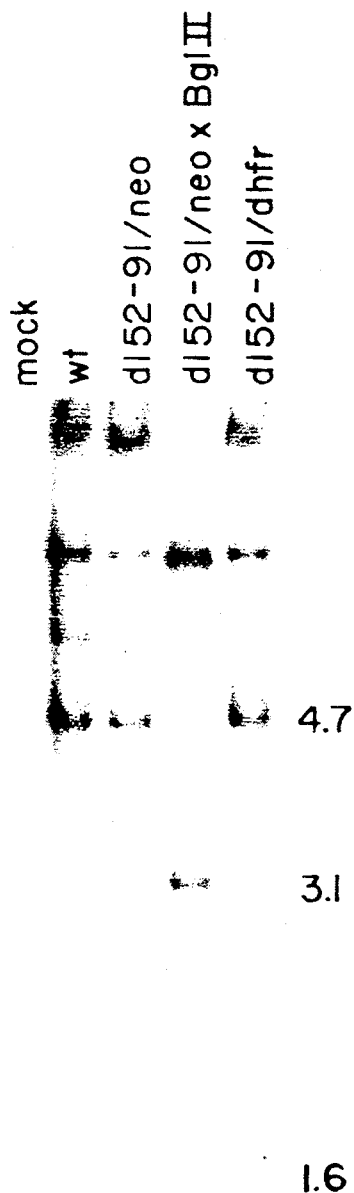
FIG. 4 sets forth the transducing virus titer determination.

To eliminate the packaging bias an AAV plasmid was constructed that was too large to be packaged. This was done by inserting a 1.1 kb fragment of bacteriophage λ DNA into a nonessential region of AAV at mu 96. The resulting plasmid ins96/λ-M (FIG. 1) contained all of the AAV coding regions intact. When the ins96/λ-M and dl52-91/neo plasmid DNAs were transfected into human cells at a 10:1 ratio, viral stocks were obtained which were enriched for the dl52-91/neo transducing virus (FIG. 4). Although the neo viral stocks contained none of the complementing ins96/λ-M genome, a variable number of the virions apparently contained wild type AAV DNA. The appearance of the wild type genome was presumably the result of recombination between ins96/λ-M and dl52-91/neo. Recombination between two complementing AAV mutants following DNA transfection had been observed previously and was expected [Hermonat et al (1984), supra].

Specifically, the hybrid virus stock was isolated as follows: Five μg of dl52-91/neo or dl52-91/dhfr plasmid DNA and 0.5 μg of ins96/λ-M plasmid DNA were co-transfected into Ad2-infected [multiplicity of infection (moi=5)] KB or 293-31 cells using DEAE dextran as described by Muzyczka, supra. The transfected cells were treated with 0.1 mM chloroquin diphosphate [Lutheman et al, Nuc. Acids Res. Vol. 11, pp. 1295-1308 (1983) for four hours (KB cells) or 20 min. (293-31 cells). Two days after transfection, the cells were frozen and thawed twice and passed through a 0.45 μm filter to remove cellular debris. The contaminating AD2 helper virus was inactivated by heating the virus stock at 56° C. for two hours to isolate the AAV recombinant virus stock.

The dl52-91/neo viral stocks were titered by comparing the yield of replicating recombinant AAV DNA obtained following infection of human cells against wild type infections using a titered AAV viral stock (FIG. 4). The wild type stock, in turn, was titered by immuno-fluroescent focus formation using anti-AAV capsid antibody [Carter et al, supra]. This rather indirect approach to titering recombinant stocks was necessary because AAV does not plaque by itself and also because only AAV anti-capsid antibodies are currently available. As shown in FIG. 4, the titer of the dl52-91/neo stocks varied depending on the host cell that was used to grow them and on the input ratio of neo to complementing plasmid DNA (not shown). One of the stocks, dl52-91/neo (KB), was estimated to have approximately $10^6$ infectious units/ml of dl52-91/neo virions and $2 \times 10^5$ infectious units/ml of wild type AAV (FIG. 4). This stock was chosen for further experiments. As expected, there was less success in obtaining a high titer dl52-91/dhfr stock, presumably because this DNA was larger than wild type size.

Although the AAV hybrid vector isolated in this case was based on the dl52-91 genome, the same procedure can successfully be applied to hybrid vectors in which the AAV genome consists of dl3-94 (FIG. 1) or any AAV deletion that retains the first and last 145 base pairs of the AAV genome. The advantage of these larger deletions is that they allow additional room for the insertions of foreign DNA. As in the case of dl52-91, ins96/λ-M (or a comparable hybrid recombinant plasmid that contains all of the AAV coding regions intact) can be used to complement dl3-94. The reason why AAV based hybrid vectors must retain the first and last 145 bp of the AAV genome is that this portion of the AAV genome is absolutely required in cis for AAV DNA replication [Samulski et al (1983), supra].

EXAMPLE 3

Transduction of Mammalian Cells by Hybrid Gene Vector (i.e., Hybrid Virus Stock)

D6, KB, and Ltk⁻ cells were placed at $10^2$ to $10^5$ cells/dish. Cells were infected with dl52-91 neo virus 12-24 hours after plating and selected for drug resistance at 12-24 hours or 7 days post-infection. D6 and KB cells were selected with 1 mg/ml Geneticin, G418 sulfate [Colbere-Garapin et al, supra]; L cells were selected at 0.4 mg/ml. These antibiotic concentrations were chosen because they killed all of the uninfected cells in 6-10 days. Cells were fed every 3 to 4 days. At 8 to 14 days post-selection cells were fixed with ethanol, stained with Giemsa and counted.

Human D6 cells were infected at various multiplicities of infection (moi) (0.1-1000). When the G418 drug selection was applied at 12-24 hours after AAV neo infection, the frequency of transduction in D6 cells appeared to be approximately 1% (Table 1). Furthermore, the transduction frequency was relatively constant with respect to the moi. A $10^4$ fold increase in moi produced an 8-fold increase in transduction. The other two cell lines, human KB cells and mouse Ltk⁻ cells, were also transduced, although at a somewhat lower frequency.

To determine whether the frequency of transduction might be a function of the time at which selection was applied, human D6 cells were allowed to incubate for 7 days after infection before G418 was added to the media. When this was done, the frequency of transduction was 10% (Table 1).

The AAV deletion genome dl3-94 was tested in a manner similar to that used for dl52-91. Briefly, the SV40 and neo sequences that had been inserted into dl52-91 above, were also inserted (by ligation) into the single BglII site of dl3-94. A hybrid vector stock or virus stock was obtained by transfection of the dl3-94-neo genome in a manner identical to that used for dl52-91/neo and the dl3-94/neo hybrid vector was then used to transduce human d6 or KB cells. The transduction frequencies obtained were similar to those seen with dl52-91/neo.

TABLE 1

| Cell Line | G418 Transducing Virus (moi) | Selection Time Days | Transduction* Efficiency (%) |
|---|---|---|---|
| D6 | 0.1 | 1 | 0.4 (.04) |
| D6 | 1 | 1 | 0.6 (0.4) |
| D6 | 100 | 1 | 1.3 (1.3) |
| D6 | 1000 | 1 | 3 |
| D6 | 1000 | 7 | 10 (10) |
| KB | 1 | 1 | 0.1 (0.07) |
| Ltk⁻ | 0.4 | 1 | 0.05 (.02) |

*Transduction efficiency equals the number of G418 resistant colonies divided by the number of infected cells. At low moi, the number of infected cells was calculated by using the Poisson distribution. Numbers in parentheses indicate the number of transductants divided by the number of cells seeded on the plate regardless of the moi. The indicated cells were seeded at $10^2$, $10^3$ or $10^5$ cells/dish and infected at the indicated moi. G418 selection was applied at the indicated times after infection (1 mg/ml for human cells or 0.4 mg/ml for murine cells). Colonies were stained with Geimsa and counted at days 8-14.

In a separate experiment human D6 cells ($10^5$) were infected with dl52-91/neo virus at a moi of 10, allowed to grow to confluence in the presence of G418 and, then, passaged twice in the presence of the drug (approximately 15-20 generations). The resulting cells were presumed to represent a mixture of $10^3$ individual transductants. This heterogeneous cell line was then expanded further and used to determine the state of the AAV/neo DNA within the transduced cells.

Figure 5:
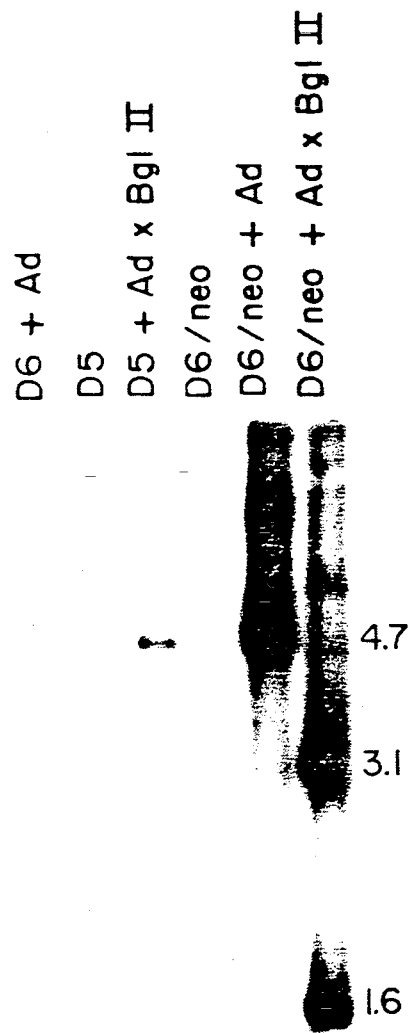
FIG. 5 shows the rescue of AAV and neo sequences from transformed cells.

Examination of the low molecular weight DNA [Hirt, supra] indicated that there were no free (low molecular weight) AAV or neomycin sequences in the G418 resistant cells (FIG. 5). This was similar to what was observed with D5 cells which are a D6-derived cell line known to be carrying a wild type AAV proviral genome (FIG. 5) [Cheung et al, supra]. This was taken to mean that infection with the dl52-91/neo virus had resulted in the transduction of G418 resistance into human cells by integration of the recombinant genome into host chromosomes to form a proviral dl52-91/neo genome. Because the G418 resistant cell line described here was heterogeneous, it was not possible to directly demonstrate the presence of the AAV recombinant proviral genome within the cellular DNA. However, 23 independent transduced clones were also isolated and in all of them, the restriction pattern of the AAV/neo proviral sequences (as determined by Southern hybridization [J. Mol. Biol., Vol. 98, pp. 503-518 (1975)] was consistent with the integration of one or more copies of the recombinant genome into host DNA.

EXAMPLE 5

Rescue of dl52-91/neo From Transduced Cells

When the D6 cells (described above) which had been transduced with dl52-91/neo virus were superinfected with Ad2 (moi = 5), the dl52-91/neo proviral sequences were rescued and amplified (FIG. 5). It will be understood that by the term "rescue", is meant the phenomenon in which proviral AAV genomes become disattached from cellular DNA and are selectively amplified by DNA replication. This has been shown to occur when cells carrying wt AAV proviruses are superinfected with Ad2 (Hoggan, supra). Digestion of the rescued DNA with BglII indicated that the bulk of the rescued sequences had the restriction pattern expected of the dl52-91/neo recombinant DNA. A small amount of wild type AAV DNA (resistant to BglII) was also seen (FIG. 5) and was, presumably, due to the fact that wild type AAV had been present in the dl52-91/neo virus stock used for the transduction. Similar results were seen when the D5 cell line was superinfected with Ad2 except that, as expected, the rescued wild type AAV sequences were insensitive to BglII digestion. Essentially, then, infection of human cells with dl52-91/neo virus produces cells carrying an AAV recombinant provirus in the same manner as occurs with wild type AAV virus infections. Similarly, the proviral AAV/neo genome behaved like integrated wild type AAV DNA in that it could be rescued by superinfection of the carrier cells with helper virus.

In the case of proviruses that consist of dl3-94 or derivatives thereof, rescue can be achieved by infection of the transduced cells with both helper virus and an AAV genome containing the rep region. The latter is required in the case of dl3-94 proviral derivatives because dl3-94 has been deleted for the AAV rep gene(s), and these are required for AAV DNA replication.

The above examples demonstrate that AAV can be used as a transducing virus for introducing foreign DNA into mammalian cells. The transductants which were isolated were due to integration of the recombinant genome into host chromosomes to form a proviral genome. Previous studies of the physical structure of wild type integrated genomes by Cheung et al, supra, and Berns, supra, suggested that AAV integrates at random positions in the host chromosomes but at a unique position with respect to its own DNA, i.e., within its terminal repeat sequence. Studies of dl52-91/neo proviral sequences indicate that recombinant AAV genomes integrate in the same way. This is quite similar to the behavior of retroviral-proviral DNA [Varmus et al, In: RNA Tumor Viruses, eds. Weiss et al (Cold Spring Harbor, New York, pp. 369-512 (1982)], but it is not clear yet whether the mechanism of integration is the same. In the above experiments, transduction frequencies of 0.4%-10% in human cells and a somewhat lower frequency in murine cells were observed. It is not clear whether these values reflect the ability of the AAV recombinant to integrate, or the ability of the neomycin gene to be expressed in these different genetic environments. The fact that the transduction frequencies were relatively constant with respect to moi, strongly suggests that a single recombinant genome is sufficient for transduction. This has been confirmed by genomic Southern blots on neomycin resistant clones isolated after low multiplicity infections.

The AAV vectors of the present invention possess a number of interesting features:

i) Expression of Integrated AAV Genomes.

Normally, integrated AAV genomes are silent. In the absence of a helper virus (i.e., Ad) there is no evidence of AAV-specific gene expression in either latently infected cells or in non-carrier cells that have been infected with AAV [Rose et al, supra; and Ostrove et al, Virology, Vol. 113, pp. 521-533 (1981)]. It is not clear whether this is due to repression of AAV transcription or translation or the need for positive activation by a helper virus-coded gene product (i.e., an adenovirus or herpes virus gene product). Whatever the reason, however, the above examples indicate that when a foreign gene is inserted into AAV it can be expressed, provided that an appropriate promoter is present. Although an SV40 promoter was used in the above examples, it will be understood that other promoters will work as well. Thus, the AAV vectors are useful for gene replacement systems in which it is desirable to have the foreign gene under the control of its own enhancer and promoter elements.

ii) Rescue of AAV Genomes.

A unique feature of integrated AAV genomes is that they can be rescued when the host cell is infected with adenovirus. This has been shown to be true, as well, of recombinant AAV DNA (FIG. 5). This illustrates an interesting aspect of AAV vectors, namely, that they can be used both for inserting and recovering foreign DNA from mammalian cells. Attempts to package the dl52-91/dhfr genome suggest that the packaging limit of AAV virions is approximately 5 kb. Genetic analysis of AAV mutants [Samulski et al (1983), supra; Hermonat et al, supra] indicates that the only cis-active sequences required for AAV rescue and replication are the terminal repeats (145 bp), and, therefore, most of the AAV genome is available for the substitution of foreign DNA. Thus, AAV will be appropriate for experiments involving the cloning and expression of mammalian cDNA fragments as well as short genomic DNA fragments.

iii) Studies of Larger DNA Fragments.

The above results show, also, that recombinant AAV DNA can be rescued from prokaryotic plasmids after DNA transfection (FIG. 3). Under these conditions, there is no apparent limit on the size of the foreign DNA insert. Up to 20 Kbp of foreign DNA have been inserted into the dl52-91/neo recombinant plasmid without significantly affecting the ability of the AAV recombinant genome to be rescued from the plasmid following transfection into human cells. This means that in the presence of helper virus, the infectious AAV plasmids can be used as transient expression vectors. Furthermore, rescue of AAV recombinants, presumably, would occur even if the plasmid DNA had integrated into a mammalian chromosome. This indicates that AAV vectors could be used in conjunction with other DNA transfer techniques (i.e., microinjection, protoplast fusion, calcium phosphate transfection) to rescue foreign DNA from mammalian cells.

iv) Host Range.

Although AAV is believed to be a human virus, its host range for lytic growth is unusually broad. Virtually every mammalian cell line which has been tried can be productively infected with AAV provided an appropriate helper virus is used [Cukor et al, In: The Parvoviruses, ed. K. I. Berns, (Plenum, New York), pp. 33-66 (1984)]. The fact that AAV has been used for the transduction of murine cells suggests that the host range for AAV integration is equally broad.

v) Gene Therapy.

AAV vectors are particularly useful for some types of gene therapy protocols. In this respect it should be noted that a) no disease has been associated with AAV-2 in either human or animal populations ([Cukor et al, supra; Ostrove et al, supra], b) integrated AAV genomes are essentially stable in tissue culture for more than 100 passages [Cheung et al, supra], and c) there is no evidence that integration of AAV alters the expression of host genes or promotes their rearrangement.

DETAILED DESCRIPTION OF THE DRAWINGS

FIG. 1 depicts the physical organization of AAV recombinant genomes.

The solid boxes indicate the position of the coding sequences for the rep, lip and cap functions of AAV. These were determined from the position of AAV mutants [Hermonat et al, supra]. The interruption in the dl52-91 line indicates the position of the deletion in this mutant. dl52-91 also has a single BglII site which has been inserted in place of the deleted sequences. dl52-91/neo contains the SV40 origin and promoter sequences (SV40 mu 71-65), stippled box) and the neomycin resistance gene sequences (striped box) inserted in dl52-91. In the process of constructing dl52-91/neo the BglII site in the vector was lost (see FIG.2). The arrow indicates the single BglII site (within the $neo_r$ sequence) which is present in the construct. dl52-91/dhfr was constructed by inserting the SV40/dhfr sequences from the plasmid pSV2-dhfr [Subramani et al, supra] into dl52-91 (see FIG. 2). Stippled boxes represent SV40 sequences, the open box represents the mouse dhfr coding sequence, and the arrow indicates a unique BglII site. Ins96/λ-M was constructed by inserting a 1.1 kb bacteriophage λ fragment (open box) into the single BglII site of ins96. Also shown is a map of dl3-94; the interruption in the dl3-94 line indicates the position of the deletion.

FIG. 2 shows the construction of AAV recombinants.

The diagram illustrates the intermediate steps in the construction of dl52-91/neo (or G418r). Arrows indicate the derivation of each plasmid as well as the restriction enzymes which were used at each step. For example, pHM2302 was the product of a ligase reaction which contained the BamHI (B) and HindIII (H) double digest fragments of pBR-neo [Southern et al (1982), supra] and pSV2-dhfr [Subramani et al, supra]. Other enzyme designations are EcoRI*(E) and PvuII (P). As in FIG. 1, stippled boxes are SV40 sequences, open boxes are mouse dhfr sequences and striped boxes are neo sequences. Solid lines and small open boxes represent AAV coding and terminal sequences, respectively; dotted lines represent pBR322 sequences. dl52-91/dhfr was constructed by inserting the appropriate BamHI fragment from pHM2101 into dl52-91 (not shown).

FIG. 3 depicts a comparison of wt and recombinant DNA replication.

One microgram of the indicated form I super-coiled plasmid DNA was transfected into KB cells. The cells were subsequently infected with Ad2 helper virus at an moi of 5. At 24 hours, cells were lysed, treated with pronase and low molecular wt DNA was isolated by Hirt (supra) extraction. One tenth of each DNA extract was then fractionated on a 1.4% agarose gel, transferred to nitrocellulose by the method of Southern (1975, supra), and hybridized to nick-translated dl52-91/neo DNA. Where indicated, the extract was digested with BglII. The large BglII fragment (3.1 kb) of dl52-91/neo has approximately the same amount of sequence homology to the probe as the full size band of wt AAV DNA (4.7 kb). Bands which are larger than 4.7 kb are normal concatemeric replication intermediates which accumulate during AAV DNA replication and input plasmid DNA. The identity of the dl52-91/neo DNA was confirmed by digestion with restriction enzymes other than BglII (not shown).

FIG. 4 sets forth the transducing virus titer determination.

Ad2-infected D6 cells (107/plate) were either infected with known quantities of wt AAV virus of 100 μl of one of three recombinant virus stocks. At 48 hours DNA was harvested, digested with BglII, and analyzed as in FIG. 3. Each lane represents 10% of the DNA recovered from one 10 cm dish. The lane marked mock contains DNA from uninfected cells. dl52-91/neo (KB) and dl52-91/neo (293) were virus stocks grown in KB and 293 cells, respectively. The lanes marked AAV contain DNA from cells which had been infected with the indicated number of fluorescent focus forming units as determined by immunofluorescence. The probe was nick-translated dl52-91/neo plasmid DNA.

FIG. 5 shows the rescue of AAV and neo sequences from transformed cells.

Parenteral D6 cells, D5 cells, or D6 cells transduced with dl52-91/neo virus (D6/neo) were examined for the presence of low molecular weight AAV or neomycin sequences as described in FIG. 3. Where indicated, the cells were infected with Ad2 48 hours before DNA isolation. Also, where indicated, the extracted DNA was digested with BglII prior to electrophoresis.

Bacteria containing the various above described plasmids have been deposited with the American Type Culture Collection Rockville, Md. as follows:

| Plasmid | ACTT No. |
| --- | --- |
| Bacteria containing plasmid ins96/λ-M | 53222 |
| Bacteria containing plasmid dl3-94 | 53223 |
| Bacteria containing plasmid dl52-91 | 53224 |
| Bacteria containing plasmid dl52-91/neo | 53225 |
| Bacteria containing plasmid pSM620 | 53226. |

We claim:

1. A hybrid gene vector comprising foreign DNA ligated into an AAV genome in place of or in addition to the cap, lip or rep coding sequence thereof or in place of or in addition to an AAV DNA sequence excluding the first and last 145 base pairs, said vector being capable of transducing data foreign DNA into a mammalian cell in the presence of a promoter other than an AAV transcription promoter, and said AAV genome being cloned in a prokaryotic vector plasmid or bacteriophage vector capable of growth in prokaryotic cells or yeast plasmid vector capable of growth in fungal cells and isolating a recombinant AAV hybrid gene vector by transfection of the ligated vector into a mammalian cell, said AAV genome being the entire AAV viral DNA or a deletion mutant thereof, capable of replication upon infection of said mammalian cell when complemented in trans by an AAV gene.

2. The vector of claim 1 wherein said AAV genome is AAV-type 2.

3. The vector of claim 2 wherein said AAV genome is the deletion mutant dl52-91 or dl3-94.

4. A method of constructing a hybrid gene vector comprising ligating foreign DNA into an AAV genome in place of or in addition to the cap, lip or rep coding sequence thereof or in place of or in addition to an AAV DNA sequence excluding the first and last 145 base pairs, said vector being capable of transducing said foreign DNA into a mammalian cell in the presence of a promoter other than an AAV transcription promoter, and said AAV genome being cloned in a prokaryotic vector plasmid or bacteriophage vector capable of growth in prokaryotic cells or yeast plasmid vector capable of growth in fungal cells and isolating a recombinant AAV hybrid gene vector by transfection of the ligated vector into a mammalian cell, said AAV genome being the entire AAV viral DNA or a deletion mutant thereof, capable of replication upon infection of said mammalian cell when complemented in trans by an AAV gene.

5. The method of claim 4 wherein said AAV genome is an AAV-type 2 genome.

6. The method of claim 5 wherein said AAV genome is the deletion mutant dl52-91 or dl13-94.

7. The method of claim 4 wherein said AAV genome is cloned in the prokaryotic plasmid vector pBR322.

8. The method of claim 4 wherein said transfection is conducted in the presence of a helper virus and/or a helper AAV plasmid ins 96/λ-M each of which contain genes necessary for the replication of AAV genome or the production of AAV virus.

9. A method of transducing foreign DNA into mammalian cells comprising infecting said cells with a hybrid gene vector comprising foreign DNA ligated into an AAV genome in place of or in addition to the cap, lip or rep coding sequence thereof or in place of or in addition to an AAV DNA sequence excluding the first and last 145 base pairs, said vector being capable of transducing said foreign DNA into a mammalian cell in the presence of a promoter other than an AAV transcription promoter, and said AAV genome being cloned in a prokaryotic vector plasmid or bacteriophage vector capable of growth in prokaryotic cells or yeast plasmid vector capable of growth in fungal cells and isolating a recombinant AAV hybrid gene vector by transfection of the ligated vector into a mammalian cell, said AAV genome being the entire AAV viral DNA or a deletion mutant thereof, capable of replication upon infection of said mammalian cell when complemented in trans by an AAV gene.

10. A method of rescuing foreign DNA from mammalian cells transduced according to a method of claim 9 comprising infecting said transduced mammalian cells with helper virus containing genes necessary for the replication of the AAV genome or the production of AAV virus.

* * * * *

UNITED STATES PATENT AND TRADEMARK OFFICE
CERTIFICATE OF CORRECTION

PATENT NO. : 5,139,941

DATED : August 18, 1992

INVENTOR(S) : Nicholas MUZYCZKA; Paul L. HERMONAT; Kenneth I. BERNS; Richard J. SAMULSKI It is certified that error appears in the above-identified patent and that said Letters Patent is hereby corrected as shown below:

Column 12, Claim 1, line 6, change "data" to -- said --;

Column 13, Claim 6, line 2, change "dl13-94" to -- dl3-94 --.

Signed and Sealed this

Seventh Day of September, 1993

Attest:

BRUCE LEHMAN

*Attesting Officer*     *Commissioner of Patents and Trademarks*